United States Patent
Minowa et al.

(10) Patent No.: US 7,162,353 B2
(45) Date of Patent: Jan. 9, 2007

(54) AUTOMOTIVE CONTROL APPARATUS AND METHOD

(75) Inventors: Toshimichi Minowa, Mito (JP); Tatsuya Ochi, Hitachi (JP); Satoru Kuragaki, Hitachi (JP); Mitsuo Kayano, Hitachi (JP); Tokuji Yoshikawa, Hitachi (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 10/768,085

(22) Filed: Feb. 2, 2004

(65) Prior Publication Data

US 2004/0153233 A1 Aug. 5, 2004

Related U.S. Application Data

(63) Continuation of application No. 09/820,533, filed on Mar. 30, 2001, now Pat. No. 6,792,344, which is a continuation of application No. 09/640,008, filed on Aug. 17, 2000, now Pat. No. 6,434,472, which is a continuation of application No. 09/066,584, filed on Apr. 27, 1998, now abandoned.

(30) Foreign Application Priority Data

Apr. 25, 1997 (JP) .................. 9-108584

(51) Int. Cl.
 *B60K 31/00* (2006.01)
 *B60L 15/20* (2006.01)
(52) U.S. Cl. ............... 701/96; 701/84; 123/339.23
(58) Field of Classification Search ............ 701/96, 701/84, 87, 91, 53, 54, 61, 65, 70, 208, 103, 701/110, 64, 58; 123/339.23, 406.64, 480; 477/115, 109, 110, 54
See application file for complete search history.

(56) References Cited

U.S. PATENT DOCUMENTS

| 4,591,986 A | * | 5/1986 | Nakajima et al. ........... 364/426 |
| 4,663,991 A | * | 5/1987 | Nakamura et al. ............ 477/49 |
| 4,720,793 A | * | 1/1988 | Watanabe et al. ........ 364/424.1 |
| 4,784,021 A | * | 11/1988 | Morimoto ..................... 477/40 |
| 4,862,854 A |   | 9/1989 | Oda et al. |

(Continued)

FOREIGN PATENT DOCUMENTS

EP 0286103 10/1988

(Continued)

OTHER PUBLICATIONS

European Search Report dated Dec. 5, 2005.

*Primary Examiner*—Dalena Tran
(74) *Attorney, Agent, or Firm*—Crowell & Moring LLP

(57) ABSTRACT

An apparatus and a method for controlling an automotive vehicle are disclosed, in which a control amount for securing safety of the vehicle and the control amount for achieving a state intended for by the driver of the vehicle are switched in such a manner as to reduce the shock due to the change in the torque generated from the power train, thereby accomplishing both safety and maneuverability at the same time. A first target value is set for controlling at least selected one of the driving torque, the driving force and the acceleration/deceleration rate. A second target value is calculated in accordance with the drive mode intended for by the driver or the driving environment ahead of the vehicle. In the case where a deviation exceeding a predetermined value develops between the first target value and the second target value, the fluctuations of at least one of the driving torque, the driving force and the acceleration/deceleration rate are suppressed.

12 Claims, 13 Drawing Sheets

U.S. PATENT DOCUMENTS

| | | | |
|---|---|---|---|
| 4,899,280 A * | 2/1990 | Onari et al. | 364/431.05 |
| 4,989,149 A * | 1/1991 | Mimura et al. | 701/95 |
| 5,048,631 A * | 9/1991 | Etoh | 180/179 |
| 5,069,181 A * | 12/1991 | Togai et al. | 123/399 |
| 5,088,043 A * | 2/1992 | Akishino et al. | 701/93 |
| 5,233,530 A * | 8/1993 | Shimada et al. | 701/107 |
| 5,234,071 A * | 8/1993 | Kajiwara | 180/169 |
| 5,382,205 A * | 1/1995 | Togai et al. | 477/43 |
| 5,392,215 A * | 2/1995 | Morita | 364/426.04 |
| 5,408,411 A * | 4/1995 | Nakamura et al. | 364/424.01 |
| 5,508,923 A * | 4/1996 | Ibamoto et al. | 364/426.01 |
| 5,517,410 A * | 5/1996 | Nakagawa et al. | 701/51 |
| 5,580,331 A | 12/1996 | Shiraishi et al. | |
| 5,605,131 A * | 2/1997 | Ohno et al. | 123/399 |
| 5,625,558 A * | 4/1997 | Togai et al. | 364/426.041 |
| 5,646,851 A * | 7/1997 | O'Connell et al. | 364/426.041 |
| 5,663,880 A * | 9/1997 | Saur et al. | 701/93 |
| 5,749,804 A * | 5/1998 | Toukura | 477/47 |
| 5,752,214 A * | 5/1998 | Minowa et al. | 701/111 |
| 5,758,306 A * | 5/1998 | Nakamura | 701/93 |
| 5,826,208 A * | 10/1998 | Kuroiwa et al. | 701/54 |
| 5,839,534 A * | 11/1998 | Chakraborty et al. | 180/169 |
| 5,895,435 A * | 4/1999 | Ohta et al. | 701/59 |
| 5,947,224 A * | 9/1999 | Kouno | 180/248 |
| 5,983,154 A * | 11/1999 | Morisawa | 701/56 |

FOREIGN PATENT DOCUMENTS

| | | |
|---|---|---|
| JP | 6-207660 | 7/1994 |
| JP | 7-47862 | 5/1995 |
| JP | 7-189795 | 7/1995 |
| JP | 8-304548 | 11/1996 |

* cited by examiner

AUTOMOTIVE CONTROL APPARATUS AND METHOD

BACKGROUND OF THE INVENTION

The present invention relates to an automotive control apparatus and method, or more in particular an apparatus and a method for controlling the output of a power train including an engine, a transmission and driving wheels in accordance with the intention of the driver and the result of recognition of other vehicle running immediately ahead.

A conventional technique for changing the drive mode of an automotive vehicle in accordance with the conditions of other vehicle running immediately ahead or the intention of the driver of vehicle is described in Japanese Patent Application Laid-open No. JP-A-47862. This patent publication discloses a method of switching the drive mode of a vehicle in accordance with the driving condition of other vehicle running immediately ahead or in accordance with the intention of the driver of the concerned vehicle, as selectively judged by the driver of the following vehicle. In other words, the driver of the own vehicle determines one of the two drive modes by his or her own judgment so that the driver can drive his or her vehicle with the driving force as intended.

Establishment of a technique for detecting the distance between and relative speeds of one vehicle and another vehicle running immediately ahead (including an obstacle lying ahead) by use of a radar for securing the safety of the following vehicle is an urgent current problem. In the prior art described above, it is indispensable to attain the drive mode intended by the driver (the linear feeling of acceleration corresponding to the accelerator pedal stroke) and to secure the safety (collision prevention) at the same time.

In the conventional method of controlling the drive mode of a vehicle which still finds applications, however, primary emphasis is always placed on the intention of the driver. Therefore, it is technically difficult to automatically switch the drive mode of a following vehicle taking both the safety of the particular following vehicle and the driving condition of a vehicle running immediately ahead into consideration. This switching operation has hitherto been left to the manipulation of the driver of the following vehicle. As a result, if the difference is large between the calculated control parameter values of the above-mentioned two drive modes, the torque changes so abruptly that an unexpected acceleration/deceleration change occurs unavoidably against the will of the driver of his own vehicle.

In the prior art, assume, for example, that the driver who has so far maintained the accelerator pedal stroke at a low value switches to a mode corresponding to the driving condition of a vehicle running immediately ahead, i.e. a mode for chasing the vehicle running immediately ahead. A deviation occurs between a target value intended for by the driver of the vehicle and an actual target control value for the chasing operation, thereby causing an undesirable torque change uncomfortable to the driver of the vehicle.

JP-A-7-189795 and JP-A-8-304548 disclose that an engine and a transmission are controlled with the control parameter such as a driving torque at a output shaft of the transmission.

SUMMARY OF THE INVENTION

The object of the present invention is to provide an automotive control apparatus and control method, in which a control amount for securing the safety of a vehicle and a control amount for attaining a mode intended for by the driver of the vehicle can be switched while reducing the shock from the power train, thus making it possible to secure the safety and the maneuverability of the vehicle at the same time.

The present invention provides an automotive control apparatus, in which fluctuations of at least selected one of the driving torque, the driving force and the acceleration/deceleration rate are suppressed in the case where a deviation beyond a predetermined value occurs between a first target value before change of at least one of the driving torque, the driving force and the acceleration/deceleration rate and a second target value calculated in accordance with the drive mode intended for by the driver or the driving environment ahead.

According to a first preferred aspect of the invention, there is provided an automotive control apparatus for setting a target value of the driving torque on the output shaft side of the transmission based on at least the accelerator pedal stroke and controlling at least the engine toque in accordance with the target value, comprising means for setting a drive mode intended for by the driver or means for recognizing the driving environment ahead, means for changing a target value in accordance with the signal produced from one of the foregoing two means, and means for suppressing the fluctuations of the driving torque in the case where a deviation of not less than a predetermined value occurs, in switching the target values, between the first target value before change and the second target value calculated according to the above-mentioned signal.

According to a second preferred aspect of the invention, there is provided an automotive control apparatus comprising means for detecting an actual vehicle acceleration/deceleration rate and means for detecting an actual vehicle speed in addition to the accelerator pedal stroke as a signal used for calculating a target value of the driving torque.

According to a third preferred aspect of the invention, there is provided an automotive control apparatus in which the torque fluctuation suppression means causes the target value change means to change the first target value first at a predetermined progressive rate for a predetermined length of time from an initial value and switches it to a second target value when the deviation between the first and second target values is reduced to a predetermined level.

According to a third preferred aspect of the invention, there is provided an automotive control apparatus, in which the torque fluctuation suppression means causes the target value change means to switch the second target value to the first target value instantaneously.

According to a fourth preferred aspect of the invention, there is provided an automotive control apparatus, in which the signal produced by the drive mode setting means or the environment recognition means represents the headway distance and the relative speed with the vehicle running immediately ahead.

According to a fifth preferred aspect of the invention, there is provided an automotive control apparatus for setting a target value of the driving torque on the output shaft side of the transmission based on at least the accelerator pedal stroke and the actual vehicle deceleration rate and controlling at least the engine torque and the transmission ratio in accordance with the target value, comprising means for calculating a target value of the rotational speed on the input shaft side of the transmission in accordance with the target value and a target rotational speed limit setting means for setting a limit to the target rotational speed on the input shaft side of the transmission.

According to a sixth preferred aspect of the invention, there is provided an automotive control apparatus for setting a target value of the driving torque on the output shaft side of the transmission based on at least the accelerator pedal stroke and the actual vehicle deceleration rate and controlling at least the engine torque and the transmission ratio in accordance with the target value, comprising means for calculating a target value of the transmission ratio in accordance with the target value of the driving torque and target transmission ratio limit setting means for setting a limit to the transmission ratio.

According to a seventh preferred aspect of the invention, there is provided an automotive control apparatus for setting at least one of the driving torque, the driving force and the acceleration/deceleration rate on the output shaft side of the transmission as a target value based on at least the accelerator pedal stroke and controlling at least the engine torque in accordance with the target value, comprising means for calculating the driving load of the vehicle, means for calculating the actual deceleration rate of the vehicle, means for calculating a target deceleration rate based on at least the deceleration rate calculated y the deceleration rate calculation means and the accelerator pedal stroke, and means for calculating the target value in accordance with the driving load calculated by the driving load calculation means and the target deceleration rate calculated by the target deceleration rate calculation means.

According to an eighth aspect of the invention, there is provided an automotive control apparatus wherein the driving load calculation means is weight rewrite means capable of rewriting the magnitude of the driving load calculated.

These means can solve the above-mentioned problems.

DESCRIPTION OF THE PREFERRED EMBODIMENTS

An embodiment of the invention will be described below with reference to the accompanying drawings.

Figure 1:
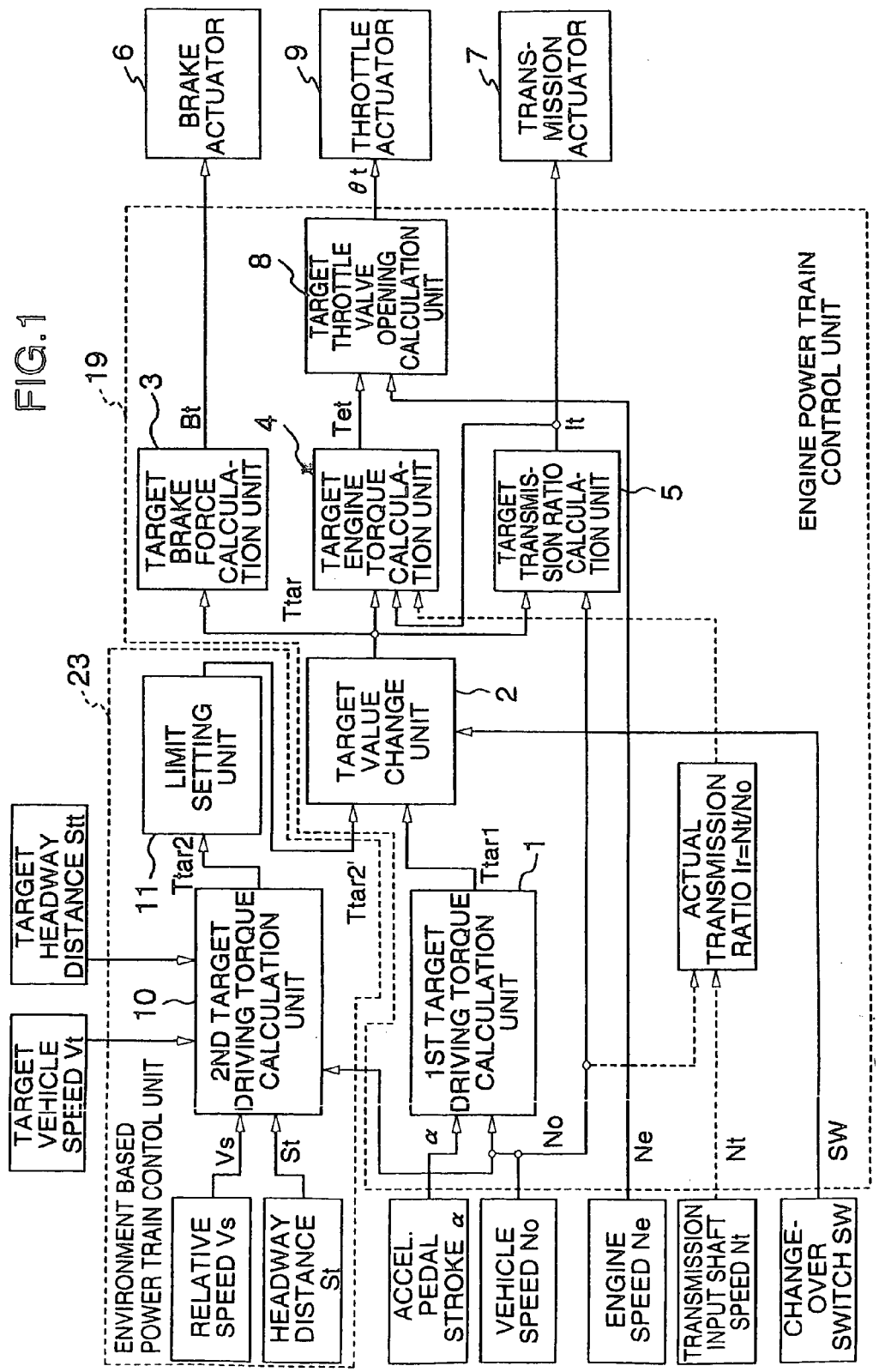
FIG. 1 is a block diagram showing the process of control according to an embodiment of the present invention.

FIG. 1 is a block diagram showing the control operation according to an embodiment of the invention. First, a control logic will be explained for the case in which an ordinary driver operates the accelerator pedal (not shown) to drive a vehicle (not shown).

The vehicle control system includes an environment based power train control unit 23, an engine power train control unit 19 and various sensors and detectors for detecting an accelerator pedal stroke, a vehicle speed, an engine speed, transmission input/output speeds, a headway distance, a relative speed, a steering angle, a throttle opening, a brake depression force and states of some switches. The environment based power train control unit 23 and the engine power train control unit 19 are formed by a microcomputer including MPU and memory devices (not shown). The MPU executes the control programs stored in the memory devices. Every function of every unit included in the environment based power train control unit 23 and the engine power train control unit 19 is implemented in accordance with the control programs.

The accelerator pedal depression stroke $\alpha$ and the vehicle speed $N_o$ are applied to a first target driving torque calculation unit 1, where a first target value Ttar1 is calculated and applied to a target value change unit 2. The first target value Ttar1 from the target value change unit 2 is directly substituted into the target value Ttar, so that the target value Ttar is applied directly to a target brake force calculation unit 3, a target engine torque calculation unit 4 and a target transmission ratio calculation unit 5.

The calculation unit 3 retrieves a brake control range composed of the target value Ttar and the target rotational speed on the transmission input shaft side thereby to calculate a target brake force Bt. This target brake force Bt is applied to a brake actuator 6 thereby to execute the brake control.

Figure 8:
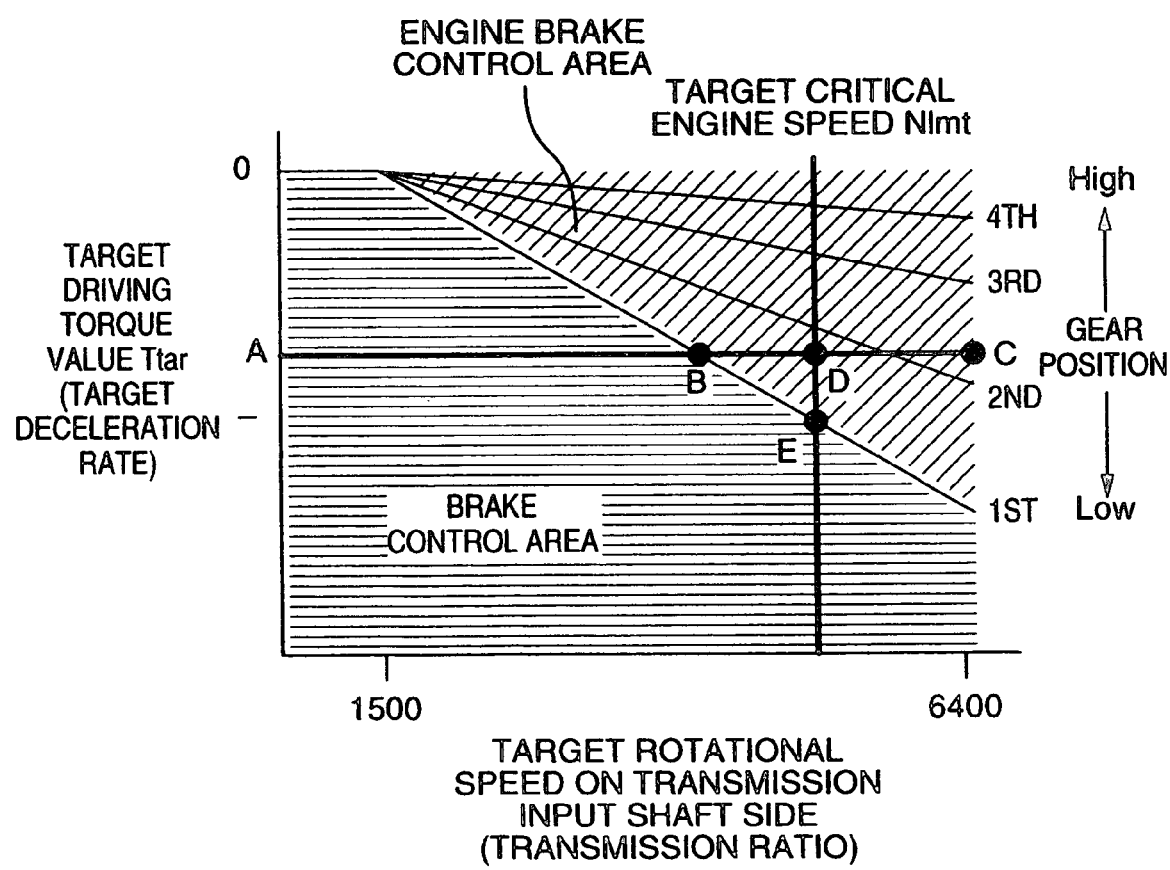
FIG. 8 is a characteristic diagram schematically showing the transmission ratio control for deceleration.

The target transmission ratio calculation unit 5 calculates a target transmission ratio $I_t$ with the target value Ttar and the vehicle speed $N_o$ as parameters during acceleration. During deceleration, on the other hand, the engine brake control area composed of the target value Ttar and the target rotational speed on the transmission input shaft side shown in FIG. 8 is retrieved thereby to calculate the target transmission ratio $I_t$. This target transmission ratio $I_t$ is applied to a transmission actuator 7 thereby to execute the acceleration control and the engine brake control.

Further, the target engine torque calculation unit 4 calculates a target engine torque Tet from the target value Ttar and the target transmission ratio $I_t$, which target engine torque Tet is applied to a target throttle valve opening calculation unit 8. A target throttle valve opening $\theta t$ is calculated and applied to a throttle actuator 9. In the process, an actual transmission ratio Ir providing the ratio between the input shaft rotational speed Nt of the transmission and the vehicle speed $N_o$ can be used in place of the target transmission ratio $I_t$, so that the ability of the actual driving torque to follow the target torque Ttar is improved for an improved torque control.

A similar effect is obtained by using the longitudinal vehicle acceleration or the driving force in place of the driving torque. Further, instead of the brake control used in the present embodiment, the engine torque and the transmission ratio can be controlled to control the acceleration/deceleration rate in a way superior to the prior art, thereby making it possible to drive the vehicle as intended by the driver.

The foregoing description concerns an automotive vehicle carrying an engine in which fuel is injected into an air inlet port. In another type of engine in which fuel is injected directly into a combustion cylinder, since larger air-fuel ratio mixture can be used by employing a combination of the throttle valve control and the fuel amount control for controlling the air-fuel ratio, therefore, a driving torque control of higher accuracy is made possible.

Now, an explanation will be given of a control logic for the case in which a constant vehicle speed control or a constant headway distance control is requested as a drive mode by the driver instead of normal drive through a drive mode changeover switch SW or the like. The term "headway distance" means a distance between a car and the one in front.

Figure 4:
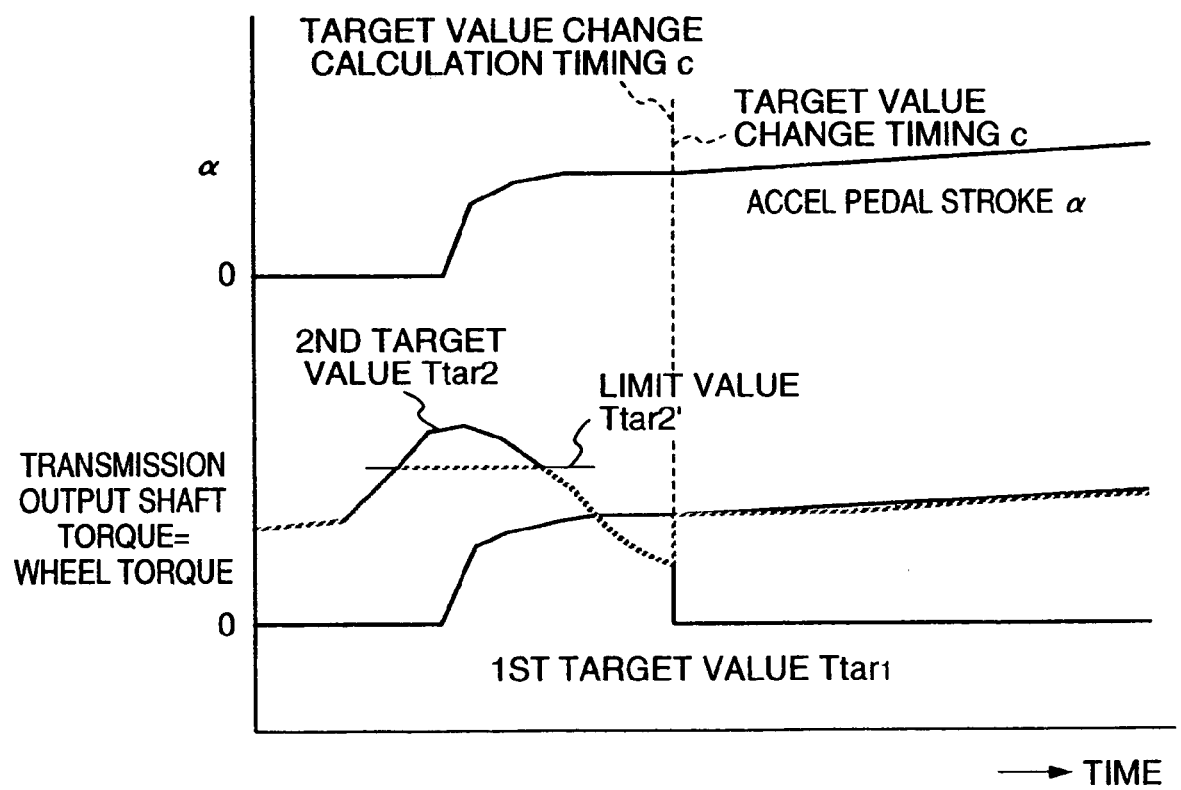
FIG. 4 is a time chart for changing a second target value to a first target value.

In FIG. 1, assume that a constant vehicle speed control is requested. A target vehicle speed Vt and a vehicle speed No are applied to a second target driving torque calculation unit 10, in which a target acceleration/deceleration rate is determined from the deviation between the target vehicle speed Vt and the vehicle speed $N_o$ and the time required for reaching the target vehicle speed Vt. Further, a second target value Ttar2 is calculated using the vehicle weight, the tire radius, the gravity and the driving resistance on flat roads of ordinary altitude. The second target value Ttar2 is applied to a limit setting unit 11. The second target value Ttar2, if it exceeds a target critical driving torque Ttar2', as shown in FIG. 4, is limited to the critical driving torque Ttar2'. As a result, an abrupt acceleration can be avoided while the vehicle is running at a constant speed. Thus, the acceleration control is possible which gives no uncomfortable feeling to the driver. Then the actuators 6, 7, 9 are driven to drive the vehicle with the critical driving torque Ttar2' or the second target value Ttar2 as a target value in place of the first target value Ttar1 for normal drive.

The target value is changed this way by the signal of the changeover switch SW. The control logic executed by the driver through the changeover switch SW incorporates a logic for changing the target value automatically in the case where the headway distance St is judged to have dangerously decreased to a considerably small value. Specifically, the driving environment in front is recognized by a radar or a camera and the result of recognition is applied to the target value change unit 2, so that the target driving torque is automatically changed from the first target value Ttar1 to the second target value Ttar2.

In the case where a constant headway distance control is requested, on the other hand, the speed Vs of a following vehicle relative to the speed of the vehicle running immediately ahead, the headway distance St with the vehicle running immediately ahead, the target head-way distance Stt with the vehicle running immediately ahead and the vehicle speed $N_o$ of the following vehicle are applied to the second target driving torque calculation unit 1. A target acceleration/deceleration rate is determined from the difference between the vehicle speed $N_o$ and the target vehicle speed Vtt determined from the relative speed Vs, the headway distance St and the target headway distance Stt relative to the vehicle running immediately ahead on the one hand and the time required for reaching a target vehicle speed on the other hand. Further, the second target value Ttar2 is calculated using the vehicle weight, the tire radius, the gravity and the driving resistance on flat roads of ordinary altitude. After that, the control operation similar to that for the above-mentioned constant vehicle speed control is performed.

A method of changing between the first target value Ttar1 and the second target value Ttar2 will be explained with reference to FIGS. 3 and 4.

Figure 3:
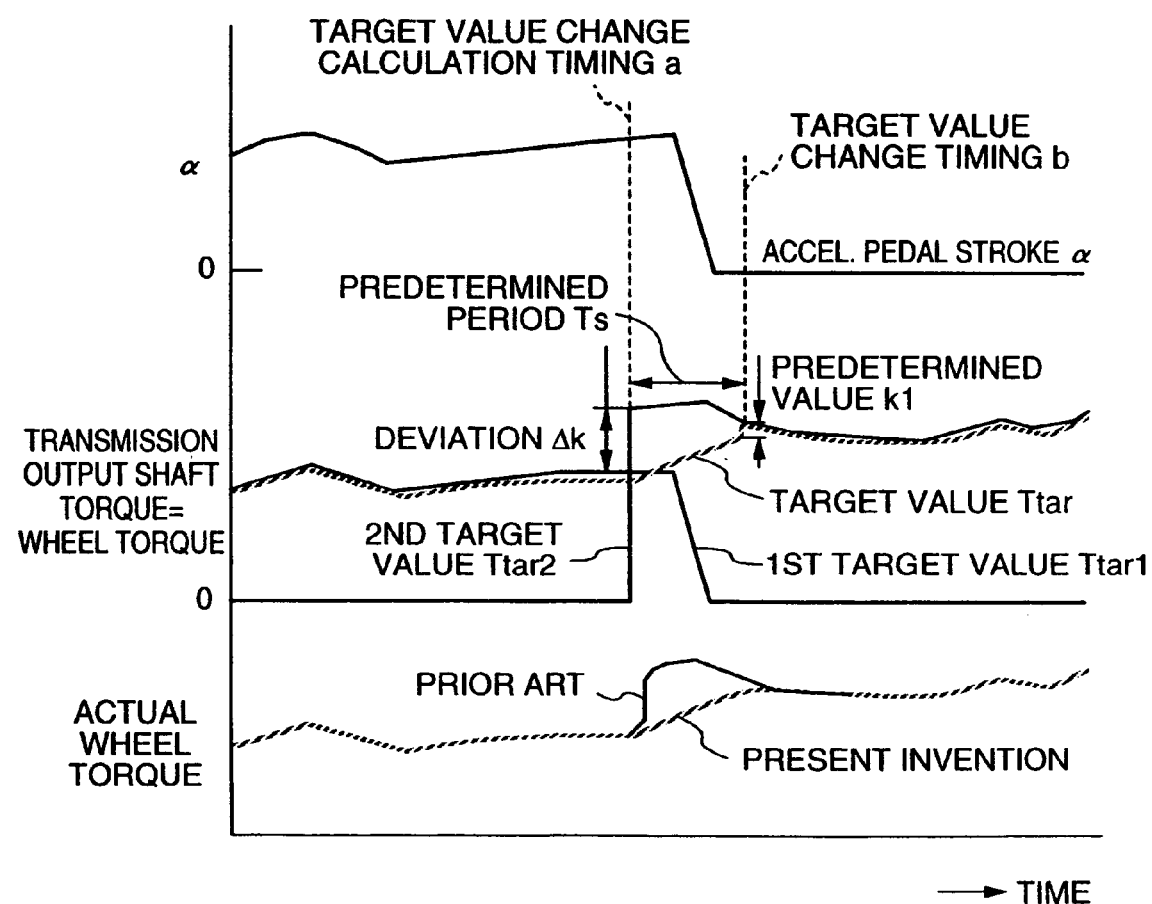
FIG. 3 is a time chart for changing a first target value to a second target value.

FIG. 3 is a time chart for changing from the first to the second target value, and FIG. 4 is a time chart for changing from the second to the first target value. In FIG. 3, consider the case in which α is larger than zero, i.e. the case in which the target value of the driving torque is changed from the first to the second value at a timing a while the vehicle is accelerating. At timing a, the second target value Ttar2 is calculated and the target is changed from the first target value Ttar1 to the second target value Ttar2. If the target vehicle speed Vt or the target vehicle speed Vtt is considerably higher than the current vehicle speed No, the deviation Δk between the first target value Ttar1 and the second target value Ttar2 assumes a large value. Consequently, once the target value is changed directly at timing a, the actual wheel torque undergoes a change (as in the prior art) to cause uncomfortable to ride.

According to the present invention, in contrast, when the target is changed from the first target value Ttar1 to the second target value Ttar2 at timing a, the target value Ttar is steadily increased before a timing b after the lapse of a predetermined time length Ts within the target change means 2, and the second target value Ttar2 is not used before the second target value Ttar2 and the target value Ttar reaches a predetermined value k1 free of torque change. As a result, the fluctuations in the actual wheel torque generated after timing a can be suppressed, thereby making possible a smooth charge in target value, i.e. a consistent transfer to a constant vehicle speed control and a constant headway distance control.

Now, in FIG. 4, consider the case in which the target driving torque is changed from the second target value Ttar2 to the first target value Ttar1 at timing c while the accelerator pedal stroke α is larger than zero, i.e. while the vehicle is accelerating. At timing c, the first target value Ttar1 is calculated from the accelerator pedal stroke α and the vehicle speed No, and the target is changed from the second target value Ttar2 to the first target value Ttar1. In this case, the intention of the driver to accelerate is given priority, and therefore the target value is changed instantaneously. Also, a time constant of about 200 milliseconds or less can be set at which the feeling of acceleration is not deteriorated.

Figure 2:
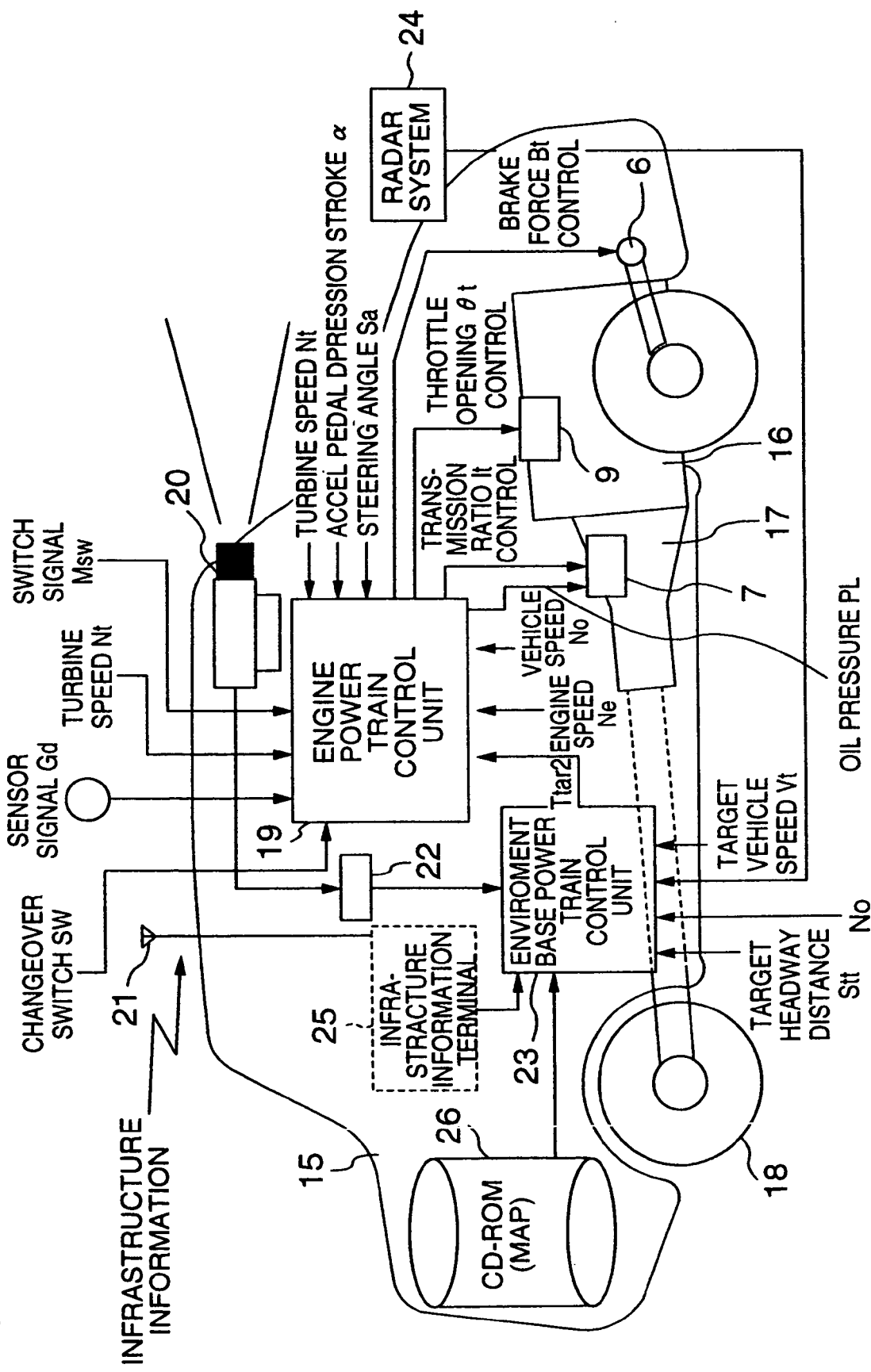
FIG. 2 is a diagram showing a system configuration according to the invention.

FIG. 2 is a diagram showing a system configuration of the invention. A vehicle body 15 has mounted thereon an engine 16 and a transmission 17. The driving force transmitted in the power train including the engine 16 and wheels 18 is controlled by an engine power train control unit 19. This engine power train control unit 19 calculates the first target value Ttar1 of the driving torque (or the driving force or the acceleration rate), and, in accordance with the target value thus calculated, further calculates a target throttle valve opening θt (or a target air flow rate), a fuel amount, an ignition timing, a brake pressure Bt, a transmission ratio It and a transmission control oil pressure PL. The fuel amount is controlled by an inlet port injection method which is currently used most widely or a direct injection method high in controllability.

The vehicle body 15 also carries a TV camera 20 for detecting the environmental conditions and an antenna 21 for receiving the information on the infrastructure. The image on the TV camera 20 is applied to and processed in an image processing unit 22 to recognize a road slope, the radius of curvature of a corner, traffic signal information, road marks, traffic control situation, other vehicles, pedestrians, obstacles, etc. A driving environment signal produced by this recognition is applied to an environment-based power train control unit 23.

Also, a radar system 24 of FM-CW type or the like is installed on the front part of the vehicle 15 to detect the distance St from or the relative speed Vs with a vehicle running immediately ahead or an object lying ahead. The antenna 21 is connected with an infrastructure information terminal 25 for supplying the infrastructure information by which to detect the conditions of the roads ahead (wet or dry, depth of water pools, snow condition, frozen or not, presence or absence of gravel, etc.), weather information (rainfall, snowfall, etc.), traffic congestion, etc. Further, from the road surface condition, the friction coefficient â⊥between the tire and the road is calculated and applied to the control unit 23.

The driving environment can also be judged from the map information stored in a CD-ROM 26 or the like, so that the road conditions ahead (slope, corner radius of curvature, traffic control, etc.) can be detected.

In the control unit 23, the second target value Ttar2 of the driving torque of the power train (or the driving force or acceleration rate) corresponding to the driving environment to be overcome is calculated on the basis of the signals representing the road slope, the corner radius of curvature, the headway distance St, the relative speed Vs, the friction coefficient $\mu$, etc. The calculation result is applied to the control unit 19.

The control unit 19 selects the first target value Ttar1 or the second target value Ttar2 according to the signal of the changeover switch SW manipulated by the driver. Assume that the second target value Ttar2 is selected. Based on this value, i.e. based on the target driving torque corresponding to the driving environment, the throttle valve opening θt, the fuel amount, the ignition timing, transmission control oil pressure PL, the transmission ratio It and the brake force Bt are calculated. Also, the control unit 19 is supplied with an accelerator pedal stroke α, a vehicle speed $N_o$, an engine speed Ne, a switch signal Msw (described later), an acceleration sensor signal Gd, a steering wheel angle Sa, etc.

Figure 5:
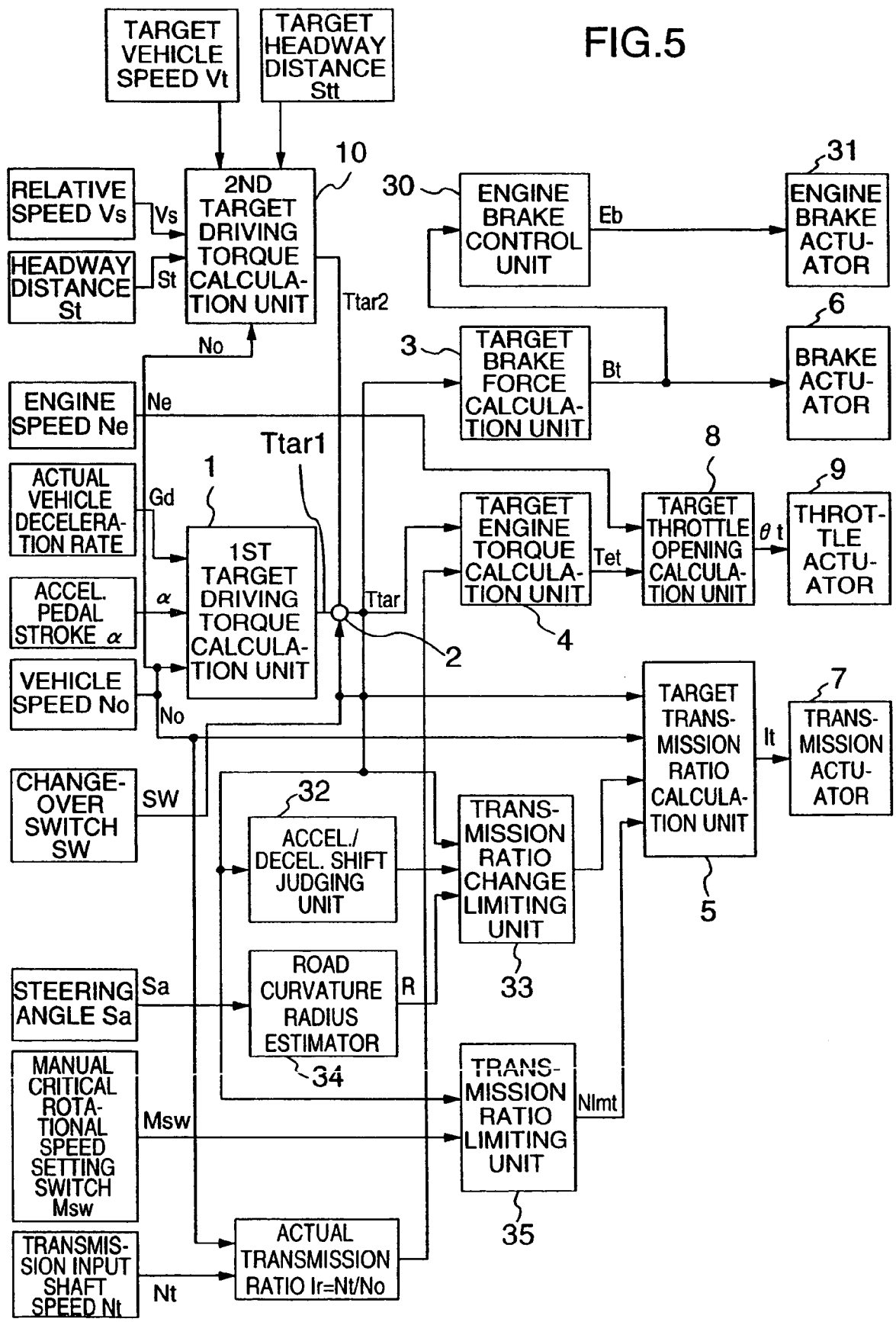
FIG. 5 is a block diagram showing the process of control according to another embodiment of the invention.

FIG. 5 is a block diagram showing the control operation according to another embodiment. The power train controller providing the base of this operation is identical to that shown in FIG. 1. The difference of this embodiment from the above-mentioned embodiment lies in the engine brake control. In FIG. 1, the engine brake is controlled by controlling the transmission ratio, while the embodiment of FIG. 5 newly includes an engine brake control unit 30 and an engine brake actuator 31. Specifically, a one-way clutch of the stepped transmission and a clutch for turning on/off the operation of the one-way clutch are used to judge whether the inverse driving force from the tires running on a descendant slope is to be transmitted or not to the engine. This system can realize a smooth deceleration control.

Figure 6:
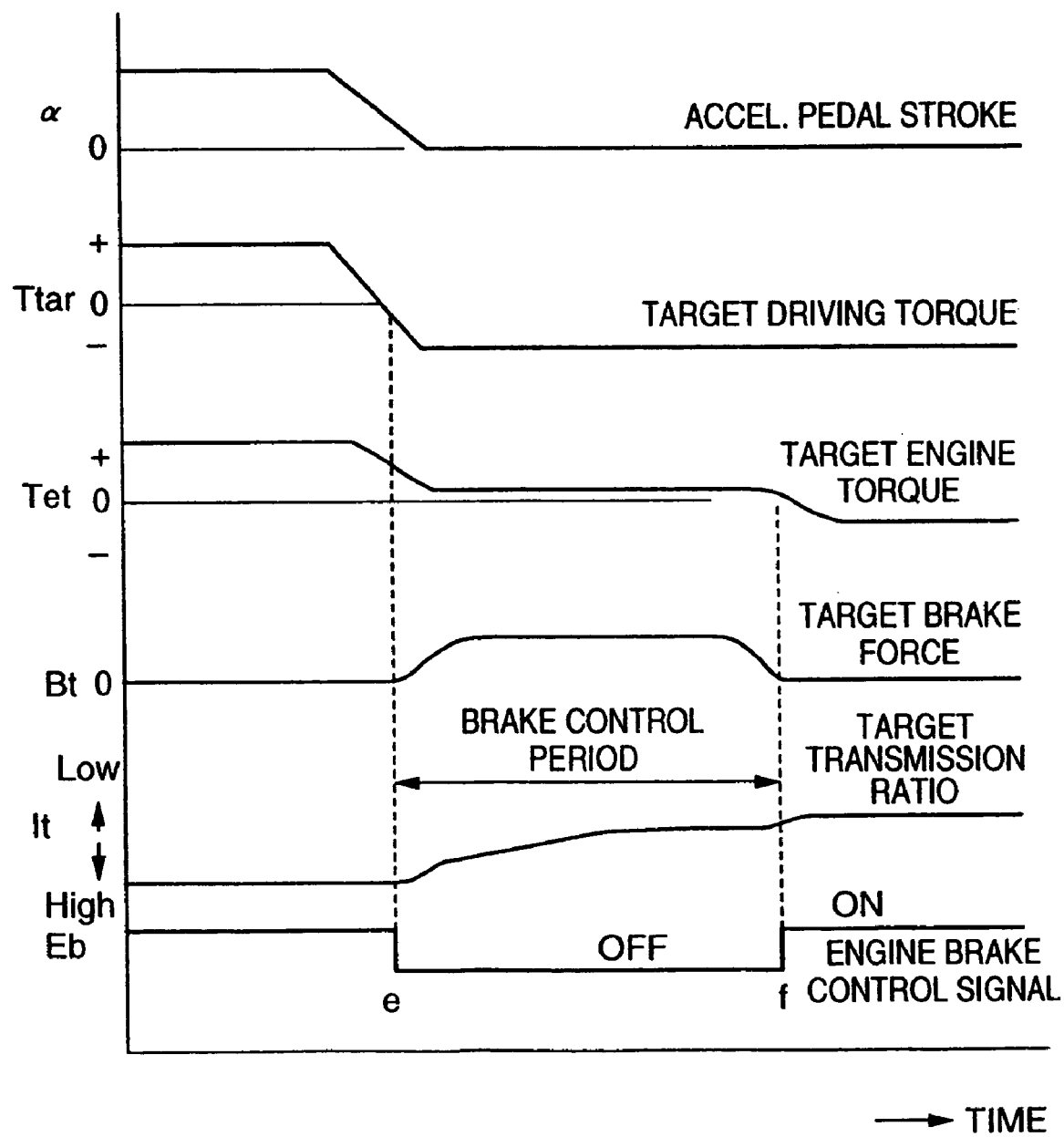
FIG. 6 is a time chart for controlling a target deceleration rate.

FIG. 6 is a time chart for the case in which the target deceleration rate is controlled as described in FIG. 5. First, a target driving torque Ttar of negative value is calculated by a combination of the accelerator pedal stroke α and the vehicle speed $N_o$ or a combination of the accelerator pedal stroke α, the vehicle speed $N_o$ and the actual vehicle deceleration rate Gd (described in detail with reference to FIG. 10). As an alternative, the target value Ttar of the driving torque is set by the second target value Ttar2 of the driving torque supplied from the environment-based power train control unit 23. In a large deceleration control requiring the brake control in accordance with this target value Ttar (period between e and f), the target engine torque Tet is set to almost zero, i.e. the vicinity of a minimum value, and further, the target transmission It is set in accordance with the value of the target engine torque Tet to achieve the target driving torque value Ttar. During the period between e and f, however, it is necessary to turn off the engine brake control signal Eb in order to avoid the feeling of deceleration which otherwise might be caused by the interference between the brake control and the engine brake control by the transmission ratio control. As a result, the deceleration is controlled only by the brake control, and therefore the controllability and the maneuverability for deceleration are improved.

Further, since the transmission ratio is shifted to the lower side (associated with a larger transmission ratio) at the time of deceleration, the feeling of acceleration is improved when actuating the accelerator pedal again.

Figure 7:
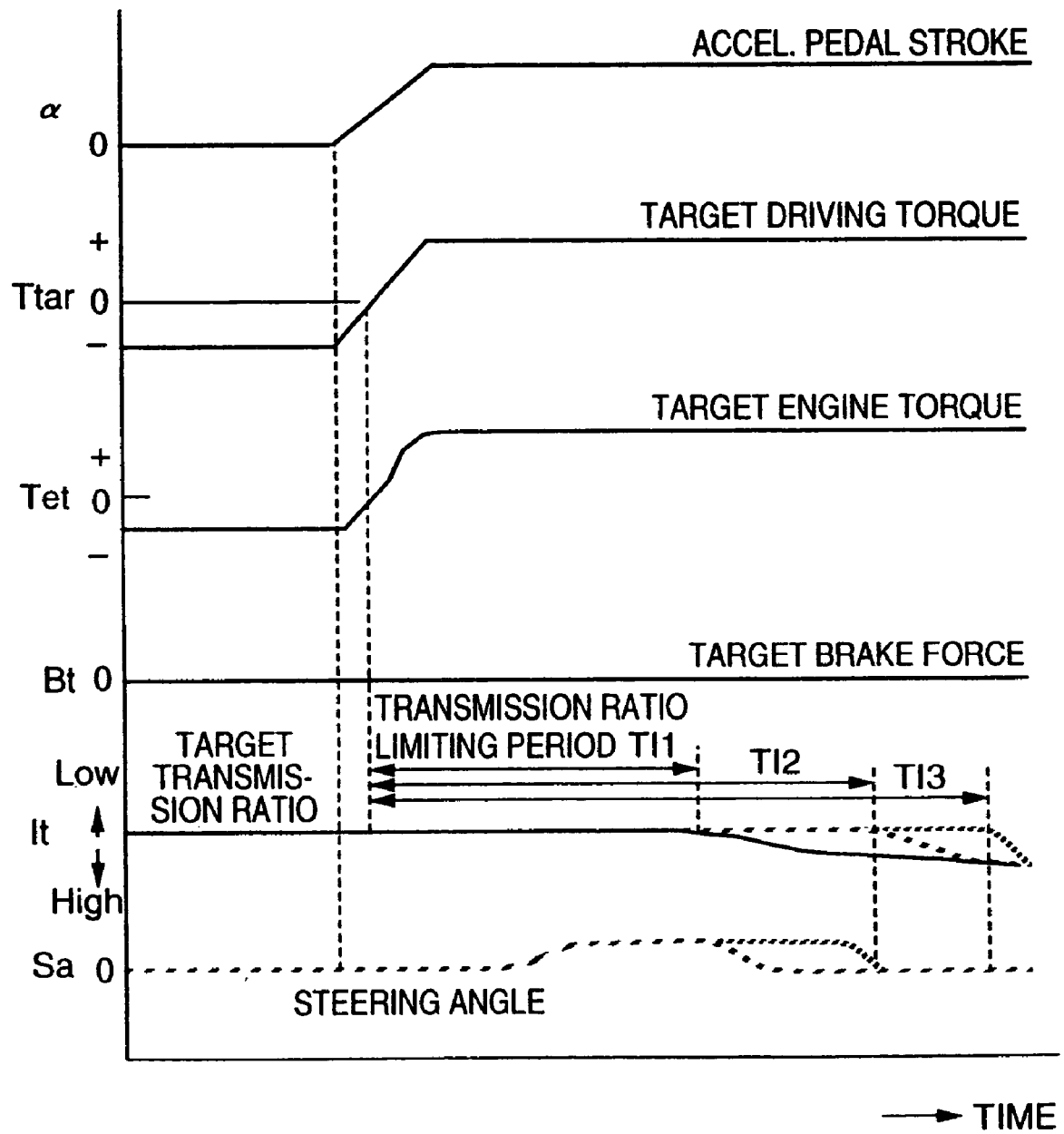
FIG. 7 is a time chart for switching between deceleration and acceleration.

Now, a method of switching from deceleration to acceleration will be explained taking the cornering control as an example with reference to FIG. 7. FIG. 7 is a time chart for the deceleration-acceleration switching control.

An acceleration/deceleration rate change judging means 32 of FIG. 5 judges whether the state in which the accelerator pedal stroke α is zero and the target value Ttar of the driving torque and the target engine torque Tet are negative has changed to the state in which the accelerator pedal stroke α, i.e. the target value Ttar of the driving torque is positive. Assume that the target value Ttar of the driving torque has turned positive and an acceleration is judged. A transmission ratio change limiter 33 holds the current transmission ratio or limits the margin of change in the transmission ratio. In view of the fact that the transmission ratio is shifted to low side (associated with a larger transmission ratio) during the deceleration, the engine speed increases at a faster rate during the acceleration (not shown), thereby improving the feeling of acceleration.

In FIG. 7, the period T11 during which the current transmission ratio is held or the margin of change in transmission ratio is limited is determined by the magnitude of the target value Ttar of the driving torque, etc. A large target value Ttar of the driving torque indicates that a large acceleration rate is required. In such a case, therefore, it is necessary to increase the holding or limiting period, as the case may be. In the case where the steering angle Sa undergoes a change during the period T11, i.e. in the case where a cornering is judged, the holding or limiting period is extended to a time point (after the lapse of period T12) when the steering angle Sa returns to zero (i.e. straight run). In the case where the cornering continues, the period can be extended to T13. Detection and judgment as to a cornering or not can be made alternatively based on the road radius of curvature R determined from the steering angle Sa (calculated by a road curvature radius estimation unit 34), a lateral acceleration sensor, a yaw rate sensor, infrastructure information, navigation information, etc. In this connection, the limited margin in the change of transmission ratio is set within ±0.5 or less so as not to adversely affect the feeling of acceleration according to this embodiment.

Now, an explanation will be given of a method of setting the transmission ratio for controlling the target deceleration rate. For acceleration, the conventional transmission ratio map or a transmission ratio taking the fuel consumption into account can be used. For deceleration, however, the requirement of engine brake makes it not an easy matter to set the transmission ratio. In the prior art, the automatic transmission fails to work as intended by the driver in this operation area of deceleration. According to this invention, the above-mentioned problem is solved using the method described below with reference to FIGS. 5 and 8.

FIG. 8 is a characteristic diagram schematically showing the transmission ratio control for deceleration. In FIG. 8, the abscissa represents the target rotational speed on the transmission input shaft side (associated with the target transmission ratio $I_t$ for a constant vehicle speed $N_o$), and the ordinate represents the target driving torque value Ttar (i.e. the target deceleration rate) of negative value.

The area along the abscissa is for brake control, and the hatched area for the transmission ratio control including the engine brake control. In the continuously variable transmission, the control level can be set arbitrarily any point over the whole hatched area. For the stepped transmission (such as a transmission having four steps of transmission ratio for forward drive), however, only the control value can be set on the solid line in the hatched portion.

First, the continuously variable transmission will be described. Assuming that the target value Ttar of the driving torque is set at point A in FIG. 8, for example, any transmission ratio on the solid line between points B and C in the hatched portion can be selected. For determining a target transmission ratio from among numerous transmission ratios, therefore, some conditions must be set. Such conditions can be the purpose of deceleration on the part of the driver, safety and fuel economy. A target critical engine speed is used as a parameter for meeting these conditions. By setting the target critical engine speed Nlmt at a value associated with point D, for example, the engine speed on the target transmission input shaft side at point D, i.e. the target transmission ratio can be determined.

Now, the stepped transmission will be explained. In this case, once the target value Ttar of the driving torque is set at point A, only the transmission ratio intersecting the point A representing the shift position of the first or second speed is selected among those transmission ratios on the four thin solid lines in the hatched portion. In the case where the target critical engine speed Nlmt is set to a value at point D as described above, however, the selection of the second speed associated with a larger value than that the one at point D is impossible, resulting in unavoidable selection of the first speed. Under this condition, however, the deceleration rate is associated with point E and the target deceleration rate cannot be achieved. Therefore, the engine torque is increased to set the target critical engine speed Nlmt to point D. The engine torque is increased by increasing the throttle valve opening or by increasing the fuel amount.

As described above, a negative transmission ratio is set based on the target value Ttar of the driving torque and the critical engine speed Nlmt, so that it is possible to solve the problem of the prior art that the automatic transmission fails to operate as intended by the driver in the deceleration range of operation. The target critical engine speed Nlmt is set in the transmission ratio limiter 35 based on the signal of the manual critical engine speed setting switch Msw shown in FIG. 5, and applied to the target transmission ratio calculation unit 5. The target transmission ratio calculation unit 5 calculates and outputs the target transmission ratio It based on the target value Ttar of the driving torque, the target critical engine speed Nlmt and the characteristic of FIG. 8 stored in a memory (not shown) or the like.

Figure 9:
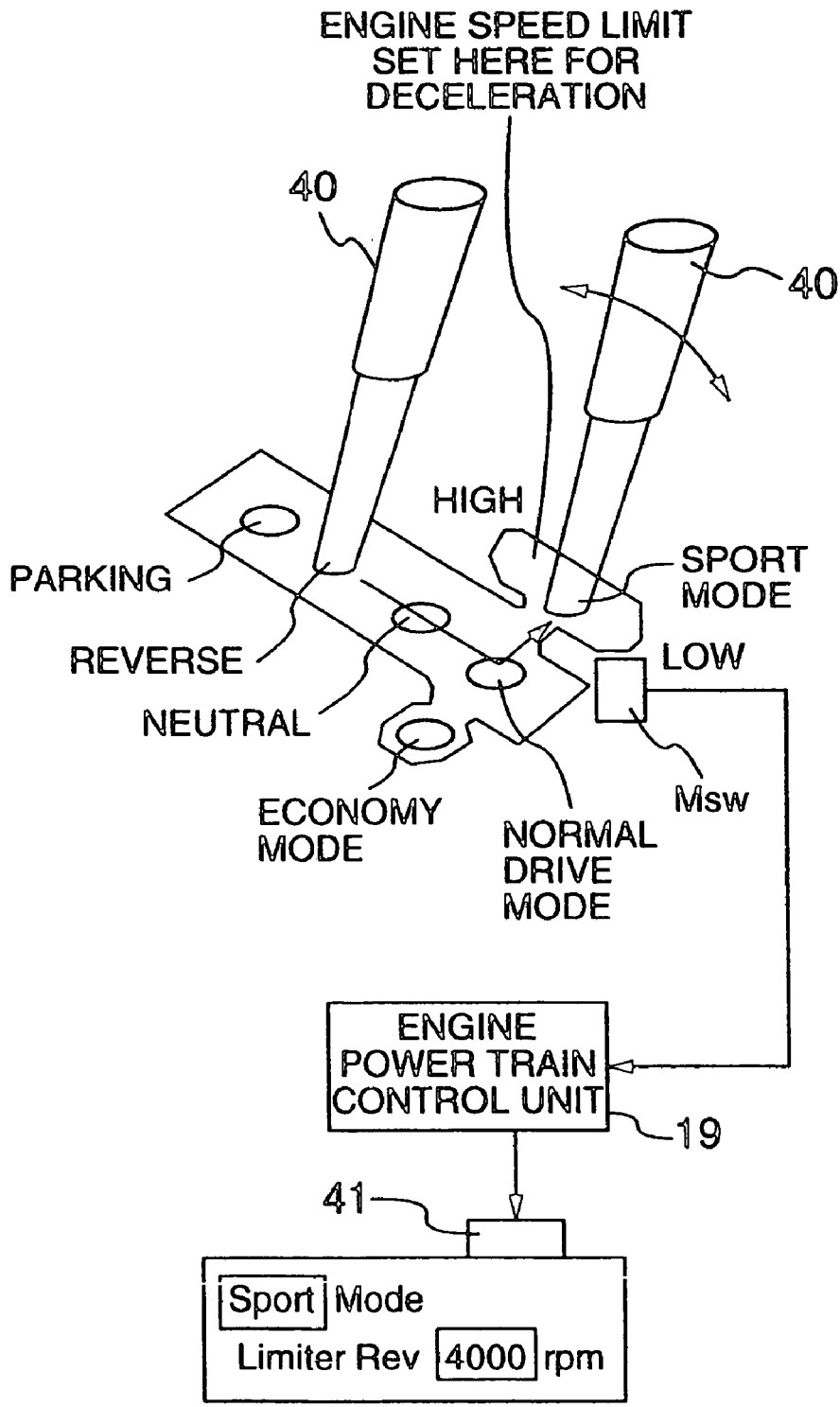
FIG. 9 is a perspective view showing a shift lever 40 for briefly explaining a method of manually setting a critical engine speed.

FIG. 9 is a perspective view of a shift lever 40 for briefly explaining a method of setting the manual critical engine speed by the manual critical engine speed setting switch Msw of FIG. 8.

The operation of the shift lever 40 can select an economy mode (EM), a normal drive mode (NDM) and a sport mode (SM). In NDM, the critical engine speed for engine brake is set at a predetermined value as low as about 1500 rpm to prevent a high deceleration rate. In ED, the fuel consumption is a more important factor than the engine speed, and therefore a transmission ratio is set taking the fuel consumption into consideration. For deceleration, the engine brake range is widened as far as possible while satisfying a target deceleration rate, and fuel supply is suspended to reduce the fuel consumption. In SM, on the other hand, the target critical engine speed Nlmt of FIG. 8 can be set by the operation of the driver. Specifically, the target critical engine speed Nlmt is increased to HIGH position or decreased to LOW position of FIG. 9 by manipulating the shift lever 40 several times repeatedly. The resulting magnitude is detected by the manual critical engine speed setting switch Msw. The signal from the manual critical engine speed setting switch Msw is applied to an engine power train control unit 19, and the target critical engine speed Nlmt is set by the transmission ratio limiter 35. Also, the target critical engine speed Nlmt is output to a display unit 41 from the engine power train control unit 19, and thus the driver is informed of the current drive mode in such a form as SPORT MODE, LIMITER REV 4000 RPM. When using the second target value Ttar2 of the driving torque, on the other hand, the acceleration/deceleration rate is controlled with stress placed on safety in whichever mode.

Figure 10:
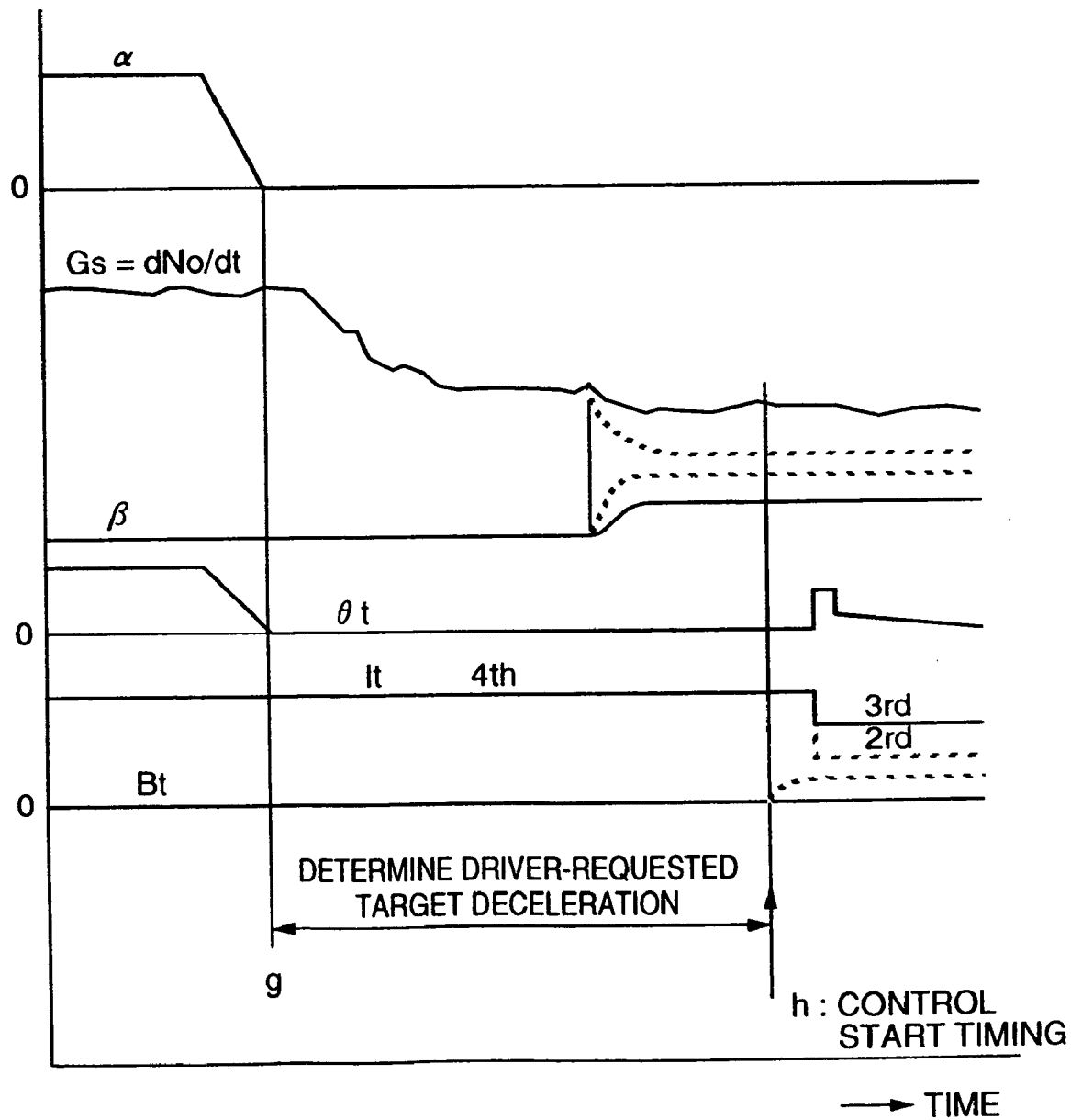
FIG. 10 is a time chart for target deceleration rate control using an actual deceleration rate Gd.

FIG. 10 is a time chart for target deceleration control using an actual deceleration rate Gd. The accelerator pedal stroke α is judged to have decreased to zero or lower, a signal representing an actual deceleration rate Gd is detected for an arbitrary length of time (period between g and h), and a target deceleration rate is calculated. Specifically, since the change in the deceleration rate Gd lags behind the change in the accelerator pedal stroke α, it is necessary to set a period of arbitrary length for deciding a target deceleration rate. In the case where the brake pedal depression force β increases during this decision period, for example, the prevailing deceleration rate Gd is used as a target deceleration rate. As a result, the power train actually starts to be controlled at time point h. The brake depression force β may be represented by a braking pressure, a brake pedal depression stroke or a signal indicative of operation of the brakes.

If the above-mentioned decision period is excessively long, however, the intention of the driver and the safety encounter a problem, whereas if the decision period is too short, judgment of the deceleration rate aimed at by the driver is difficult. It is therefore empirically proper to set the decision period at 300 ms to 800 ms.

For the stepped transmission, the target transmission ratio It is set from the fourth speed to the third speed when the brake pedal is not actuated and from the fourth speed to the second speed when the brake pedal is actuated, based on the transmission ratio control described with reference to FIG. 8. Also, the target throttle valve opening θt is controlled during the speed change in order to improve the speed change response. A detailed explanation will given below with reference to FIG. 11.

Figure 11:
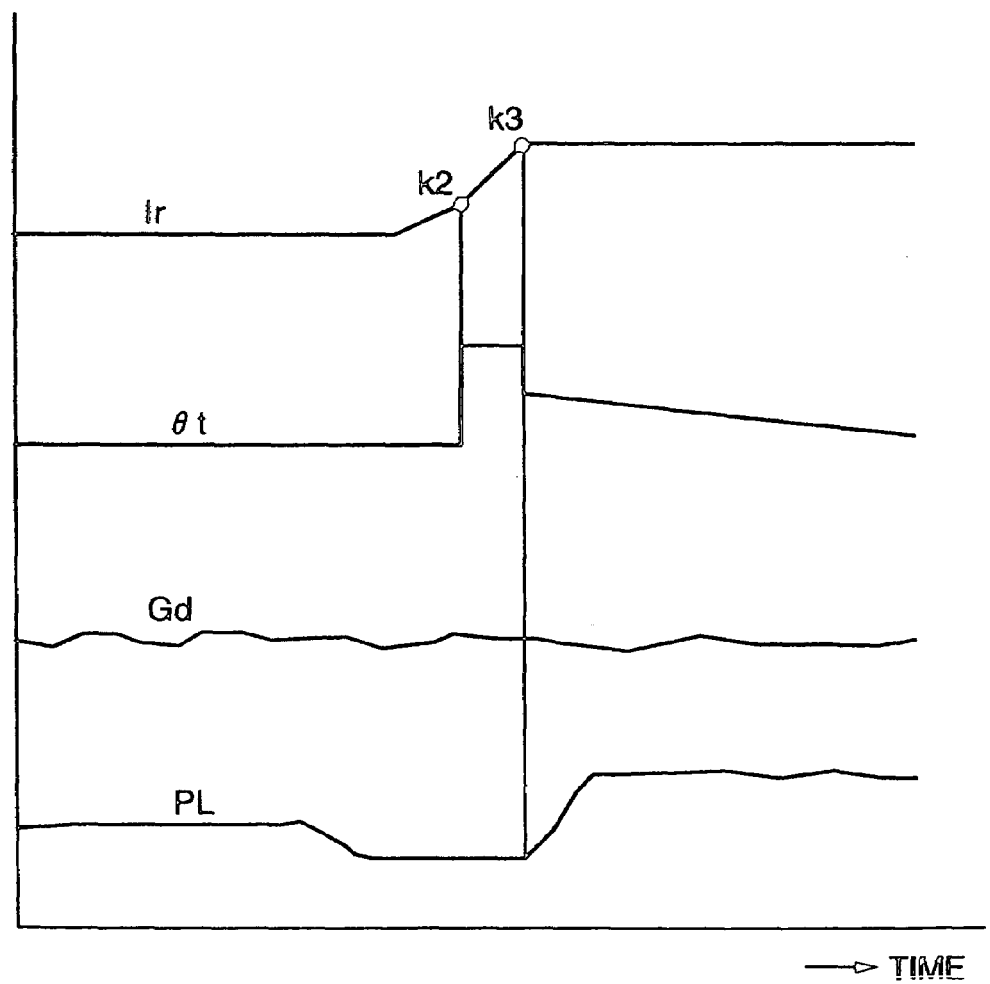
FIG. 11 is a time chart for controlling the throttle valve opening during change shift operation.

FIG. 11 is a time chart for throttle valve opening control during speed change. Especially for the stepped transmission, the transmission ratio is required to be changed in large steps, and therefore auxiliary control by the engine torque control applies effectively. Specifically, whether the speed is undergoing a change is determined using the actual transmission ratio Ir, and judgment is made as to whether the transmission ratio Ir has reached a value associated with the time k2 for starting the throttle control. In the case where the time k2 has arrived, the engine speed expected to change after speed change operation is predicted, and the throttle valve opening corresponding to the particular engine speed is calculated and output. The oil pressure PL supplied to the clutch of the transmission in the process is reduced beforehand at the time point of generation of a transmission start command signal. This makes possible a rapid shift-down operation. At time point k3, the throttle control is terminated for increasing the engine speed, and the process proceeds to the step of decreasing the target deceleration rate described with reference to FIG. 8. At the same time, an oil pressure PL corresponding to the target engine torque Tet, i.e. the target throttle opening θt is set upward. In this way, the target deceleration control makes shift-down difficult with the decrease in engine speed, and therefore makes indispensable the cooperative control of the throttle valve opening and the oil pressure shown in FIG. 11.

Figure 12:
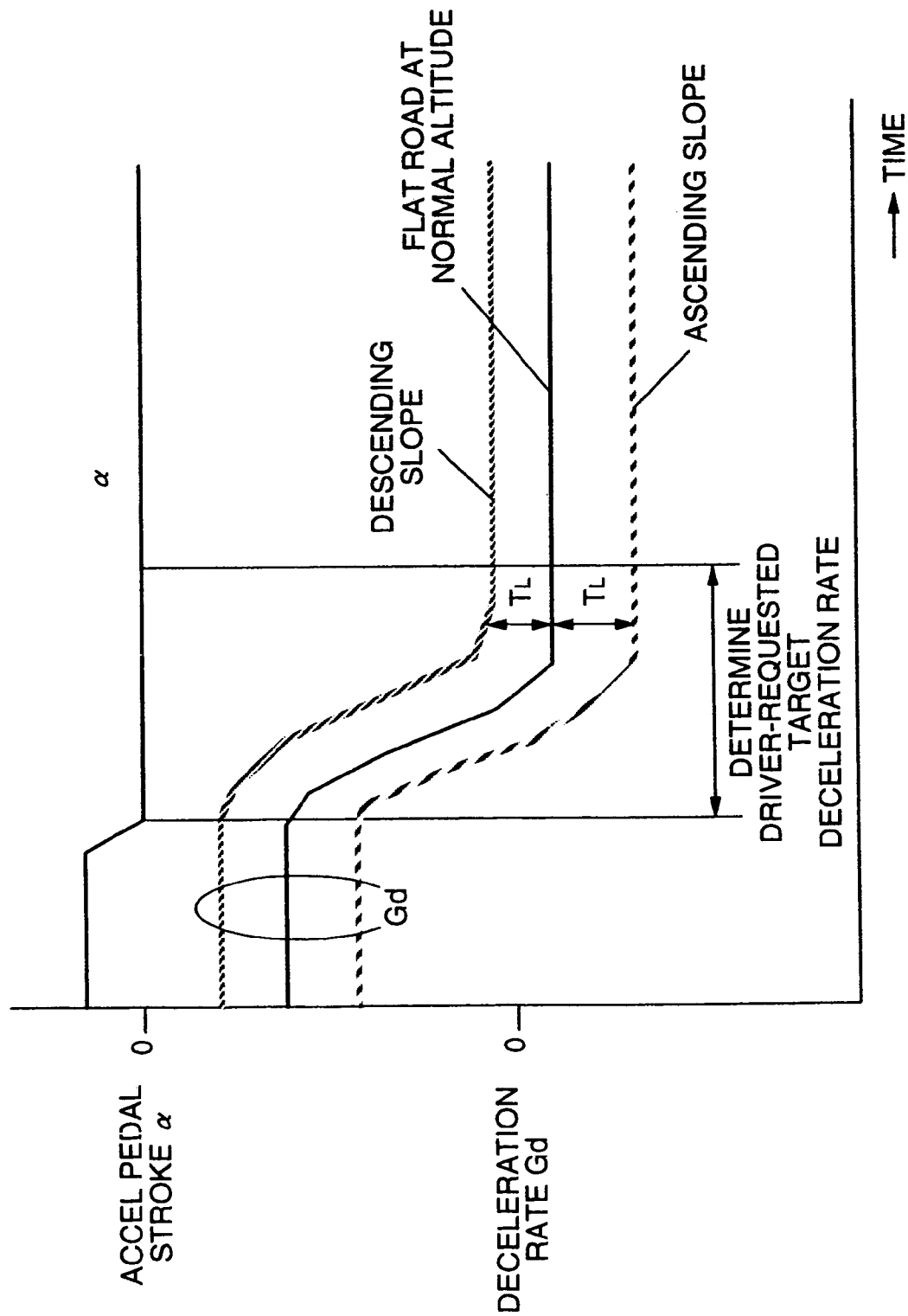
FIG. 12 is a time chart showing a deceleration rate characteristic for different road slopes.
Figure 13:
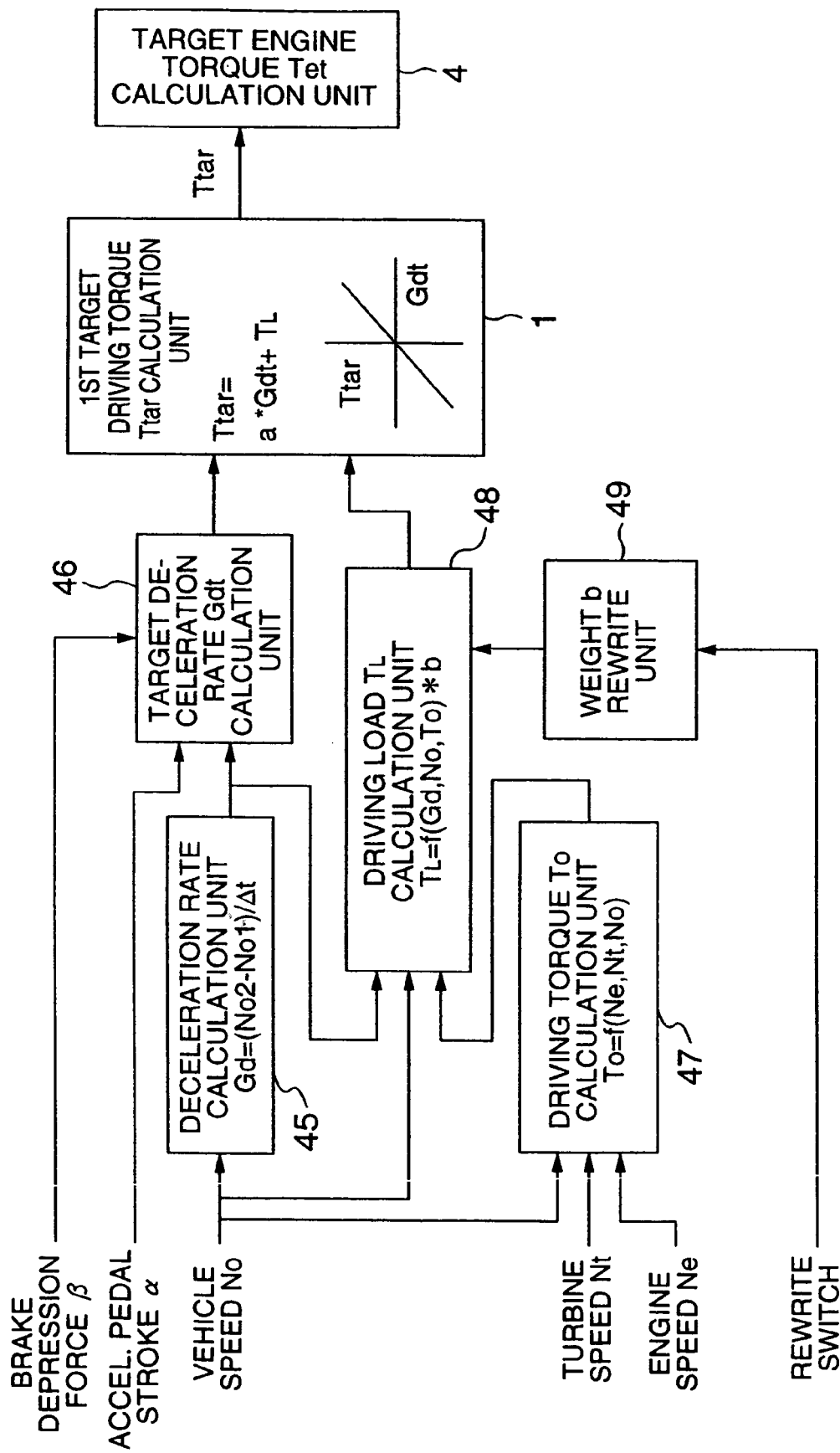
FIG. 13 is a block diagram for calculating a target value corresponding to the driving load.

FIG. 12 is a time chart showing the deceleration rate characteristic with different road slope inclinations, and FIG. 13 is a block diagram for calculating a target value corresponding to a driving load.

In FIG. 12, the solid line represents a deceleration characteristic with the accelerator pedal stroke α of zero on flat roads of normal altitude, the dotted line represents a deceleration characteristic with the accelerator pedal stroke α of zero on a descending slope, and the dashed line represents a deceleration characteristic with the accelerator pedal stroke α of zero on an ascending slope. The difference between solid line and dotted line or dashed line represents a driving load TL. As described above, the target deceleration rate is determined as required by the driver during an arbitrary length of time after the accelerator pedal stroke α is reduced to zero. Assume, for example, that the power train is controlled to achieve the actual deceleration rate when the driver has reduced the accelerator pedal stroke a to zero. This deceleration rate is the target value required by the driver.

On a descending slope, on the other hand, the driving load is reduced, and therefore, the deceleration rate is also reduced, i.e. the operation shifts toward acceleration. As a result, the driver feels uncomfortable and the different deceleration rate from the one required by the driver, and the driver apply the brakes. On an ascending slope, on the other hand, the driving load is high, and therefore the deceleration rate increases, i.e. the operation shifts towards deceleration. Consequently, the driver feels uncomfortable, and the deceleration different from the one required by the driver, and the driver actuates the accelerator pedal.

In view of this, the driving load is determined as described above, and a target deceleration rate is determined and corrected in accordance with this driving load. In this way, the acceleration control corresponding to the change in the road slope inclination is realized. The driving performance is further improved if the driving load is corrected by the age, sex, etc. of the driver.

Now, the control logic of FIG. 12 will be explained with reference to FIG. 13. First, the vehicle speed $N_o$ is applied to the deceleration rate calculation means 45 thereby to calculate the actual vehicle deceleration Gd. The deceleration rate Gd, the accelerator pedal stroke α and the brake pedal depression signal β are applied to the target deceleration rate calculation unit 46 thereby to calculate the target deceleration rate Gdt.

The target deceleration rate Gdt is calculated in the case where the accelerator pedal stroke α becomes zero and the brake pedal depression signal β changes during the target deceleration rate determining period of FIG. 12.

Then, the vehicle speed $N_o$, the turbine speed Nt and the engine speed Ne are applied to the driving torque calculation unit 47, so that the actual driving torque To is calculated. The driving torque calculation unit 47 determines the driving torque To from the torque converter characteristic and the transmission ratio undergoing an abrupt change in initial stages of the speed change. The driving torque is calculated in a similar manner to the method described in detail in JP-A-6-207660.

The driving torque To, the deceleration rate Gd and the vehicle speed $N_o$ are applied to the driving load calculation unit 48 thereby to calculate the driving load TL. In FIG. 13, the driving load TL is expressed by a functional equation. Actually, however, it can be determined from the following equation (1) for vehicle drive.

$$TL = T_o - I_V \circ Gd \qquad (1)$$

where Iv is the inertial mass of the vehicle.

Finally, the driving load TL and the target deceleration Gdt are applied to the first target driving torque calculation unit 1 thereby to calculate the first target value Ttar. This conversion equation is based on equation (1). The first target value Ttar can alternatively be determined by experiments from the actual vehicle characteristics. The calculations including and subsequent to the target engine torque calculation unit 4 are similar to the corresponding calculations in FIG. 1.

The weight b of the functional equation of the driving load calculation unit 48 of FIG. 13 will be described below.

Generally, different drivers prefer different deceleration rates on an ascending or descending slope. This deceleration rate can be freely changed according to this invention. A rewrite switch signal that can be manipulated by the driver is applied to a weight rewrite unit 49 and thus the deceleration on an ascending or descending slope can be freely changed. Specifically, the weight b calculated in the weight rewrite unit 49 is input to the driving load calculation unit 48, thereby making it possible to change the magnitude of the driving load TL.

The above-mentioned application of the control logic suppresses the fluctuations of the torque produced from the power train when switching between the control amount for securing the vehicle safety and the control amount for achieving the mode intended for by the driver. At the same time, an acceleration rate or a deceleration rate not intended for by the driver is prevented. In this way, the deceleration rate required by the driver is obtained in all driving environments including flat roads at normal altitude and ascending and descending slopes. A comfortable ride and a safety compatible with a superior maneuverability can thus be realized.

The invention claimed is:

1. A method of controlling a vehicle having a first running mode wherein a driving shaft torque of the vehicle is controlled according to a first target value determined from an accelerator pedal position, and a second running mode wherein the driving shaft torque of the vehicle is controlled according to a second target value determined from at least one of a target vehicle speed and a headway distance of said vehicle, comprising:

when said second running mode is changed to said first running mode, changing the target value of the driving shaft torque instantaneously from the second target value to the first target value, and when said first running mode is changed to said second running mode, changing the target value of the driving shaft torque smoothly from the first target value to the second target value.

2. A method according to claim 1, when said first running mode is changed to said second running mode, said method further comprising the step of setting a third target value which gradually varies from said first target value to said second target value for transition from said first running mode to said second running mode.

3. A method according to claim 2, wherein a time constant of 200 milliseconds or less is set for transition from said second running mode to said first running mode.

4. A method of controlling a vehicle having a first running mode wherein an engine torque of the vehicle is controlled according to a first target value determined from an accelerator pedal position, and a second running mode wherein the engine torque is controlled according to a second target value determined from at least one of a target vehicle speed and a headway distance of said vehicle, comprising:
    when said second running mode is changed to said first running mode, changing the target value of the engine torque instantaneously from the second target value to the first target value, and
    when said first running mode is changed to said second running mode, changing the target value of the engine torque smoothly from the first target value to the second target value.

5. A method according to claim 4, when said first running mode is changed to said second running mode, said method further comprising the step of setting a third target value which gradually varies from said first target value to said second target value for transition from said first running mode to said second running mode.

6. A method according to claim 5, wherein a time constant of 200 milliseconds or less is set for transition from said second running mode to said first running mode.

7. A control apparatus for a vehicle having a first running mode wherein a driving shaft torque of the vehicle is controlled according to a first target value determined from an accelerator pedal position, and a second running mode wherein the driving shaft torque of the vehicle is controlled according to a second target value determined from at least one of a target vehicle speed and a headway distance of said vehicle, wherein the control apparatus is configured such that,
    when said second running mode is changed to said first running mode, the target value of the driving shaft torque is changed instantaneously from the second target value to the first target value, and
    when said first running mode is changed to said second running mode, the target value of the driving shaft torque is changed smoothly from the first target value to the second target value.

8. A control apparatus according to claim 7, when said first running mode is changed to said second running mode, a third target value which gradually varies from said first target value to said second target value is set for transition from said first running mode to said second running mode.

9. A control apparatus according to claim 8, wherein a time constant of 200 milliseconds or less is set for transition from said second running mode to said first running mode.

10. A control apparatus for a vehicle having a first running mode wherein an engine torque of the vehicle is controlled according to a first target value determined from an accelerator pedal position, and a second running mode wherein the engine torque is controlled according to a second target value determined from at least one of a target vehicle speed and a headway distance of said vehicle, wherein the control apparatus is configured such that,
    when said second running mode is changed to said first running mode, the target value of the engine torque is changed instantaneously from the second target value to the first target value, and
    when said first running mode is changed to said second running mode, the target value of the engine torque is changed smoothly from the first target value to the second target value.

11. A control apparatus according to claim 10, when said first running mode is changed to said second running mode, a third target value which gradually varies from said first target value to said second target value is set for transition from said first running mode to said second running mode.

12. A control apparatus according to claim 11, wherein a time constant of 200 milliseconds or less is set for transition from said second running mode to said first running mode.

* * * * *